(12) United States Patent
Wiehl et al.

(10) Patent No.: US 11,344,532 B2
(45) Date of Patent: May 31, 2022

(54) TOPICALLY ADMINISTRABLE FORMULATION FOR THE CONTROL AND PREVENTION OF ANIMAL PARASITES

(71) Applicant: BAYER ANIMAL HEALTH GMBH, Leverkusen (DE)

(72) Inventors: Wolfgang Wiehl, Cologne (DE); Petra Ohage-Spitzlei, Leverkusen (DE); Franziska Schmidt, Duesseldorf (DE)

(73) Assignee: Bayer Animal Health GmbH, Leverkusen (DE)

( * ) Notice: Subject to any disclaimer, the term of this patent is extended or adjusted under 35 U.S.C. 154(b) by 0 days.

(21) Appl. No.: 16/644,268

(22) PCT Filed: Sep. 3, 2018

(86) PCT No.: PCT/EP2018/073620
§ 371 (c)(1),
(2) Date: Mar. 4, 2020

(87) PCT Pub. No.: WO2019/048381
PCT Pub. Date: Mar. 14, 2019

(65) Prior Publication Data
US 2021/0059986 A1  Mar. 4, 2021

(30) Foreign Application Priority Data
Sep. 6, 2017  (EP) .................................. 17189706

(51) Int. Cl.
| | |
|---|---|
| *A61K 31/4155* | (2006.01) |
| *A61P 33/14* | (2006.01) |
| *A61K 9/00* | (2006.01) |
| *A61K 31/42* | (2006.01) |
| *A61K 47/24* | (2006.01) |

(52) U.S. Cl.
CPC ........ *A61K 31/4155* (2013.01); *A61K 9/0014* (2013.01); *A61K 31/42* (2013.01); *A61K 47/24* (2013.01); *A61P 33/14* (2018.01)

(58) Field of Classification Search
CPC ........................... A61K 31/4155; A61P 33/14
See application file for complete search history.

(56) References Cited

U.S. PATENT DOCUMENTS

| | | |
|---|---|---|
| 6,001,858 A | 12/1999 | Sirinyan et al. |
| 6,372,765 B1 | 4/2002 | Sirinyan et al. |
| 9,487,489 B2 | 11/2016 | Maue et al. |
| 9,758,485 B2 | 9/2017 | Hallenbach et al. |
| 9,944,604 B2 | 4/2018 | Gorgens et al. |
| 10,150,737 B2 | 12/2018 | Hallenbach et al. |
| 10,513,496 B2 | 12/2019 | Gorgens et al. |
| 2011/0009457 A1 | 1/2011 | Gorgens et al. |

FOREIGN PATENT DOCUMENTS

| | | |
|---|---|---|
| CN | 1539285 A | 10/2004 |
| EP | 2072501 A1 | 6/2009 |
| EP | 2529620 A1 | 12/2012 |
| WO | 9617520 A1 | 6/1996 |
| WO | 2005/085216 A1 | 9/2005 |
| WO | 2009/126668 A2 | 10/2009 |
| WO | 2010/070068 A2 | 6/2010 |
| WO | 2012/120399 A1 | 9/2012 |
| WO | 2014/122083 A1 | 8/2014 |
| WO | 2015/067646 A1 | 5/2015 |
| WO | 2015/067647 A1 | 5/2015 |
| WO | 2016/144678 A1 | 9/2016 |
| WO | 2017/050921 A1 | 3/2017 |

OTHER PUBLICATIONS

International Search Report for PCT/EP2018/073620, dated Dec. 10, 2018.
WHO Drug Information, vol. 31, No. 2 (2017) 151-383.

*Primary Examiner* — Kamal A Saeed
(74) *Attorney, Agent, or Firm* — McBee Moore & Vanik IP, LLC; Susan E. Shaw Mcbee

(57) ABSTRACT

The invention relates to novel liquid formulations suitable for topical administration to animals, which formulations comprise a fluorine-containing antiparasitic active compound and also triethyl phosphate, and to their use for the control and prevention of animal parasites.

16 Claims, No Drawings

TOPICALLY ADMINISTRABLE FORMULATION FOR THE CONTROL AND PREVENTION OF ANIMAL PARASITES

CROSS-REFERENCE TO RELATED APPLICATIONS

This application is the National Stage entry of International Application No. PCT/EP2018/073620, filed 3 Sep. 2018, which claims priority to European Patent Application No. 17189706.9, filed 6 Sep. 2017.

BACKGROUND

Field

The invention relates to novel liquid formulations suitable for topical administration to animals, which formulations comprise a fluorine-containing antiparasitic active compound and also triethyl phosphate, and to their use for the control and prevention of animal parasites.

Description of Related Art

Modern fluorine-containing antiparasitic active compounds (here also referred to as fluorinated antiparasitics), for example fluralaner, afoxolaner, sarolaner, lotilaner, fipronil, which has been known for a relatively long time, and the active compounds described in WO2015/067646 and WO2015/067647 have good insecticidal and acaricidal efficacy. However, many of these active compounds have very low solubility in solvents suitable for topical administration to animals. To avoid the formulation dropping off from the coat after administration, or to avoid that the animal is left with a wet coat, the active compound should preferably be dissolved in a low volume, which means that in most cases high active compound concentrations in the order of 30% w/v are desirable. Furthermore, the solvent must be toxicologically safe and have high skin compatibility. The formulation should be odourless or have a pleasant smell. At the same time, from a production viewpoint, solvents having a high flash point of greater than 35° C. are advantageous to keep expenditure for protection against explosions to a minimum. Also, the dissolved active compound has to be sufficiently stable in the formulation.

N-Methyl-2-pyrrolidone (NMP) is a very good solvent for numerous organic compounds and is also used for spot-on formulations. However, as a result of a re-evaluation by the European Chemicals Agency ECHA (ECHA/RAC/RES-O-000000 5316-76-01/F), the use of NMP for new products has to be questioned.

Propylene carbonate and mixtures of propylene carbonate and benzyl alcohol are established as solvents with good compatibility suitable for spot-on formulations (see, for example, WO9617520). However, propylene carbonate and mixtures of propylene carbonate and benzyl alcohol have insufficient solubility for the fluorinated active compounds mentioned above.

Triethyl phosphate has hitherto not been disclosed as solvent for spot-on formulations. WO2016144678 describes triethyl phosphate as liquid thinner for oily dispersions, suspensions, emulsions and solutions.

SUMMARY

Accordingly, it was an object of the present invention to provide novel liquid medicaments for topical administration to animals using a solvent with sufficiently high solubility for modern fluorinated antiparasitics. The liquid formulation used for such medicaments should have the following properties:
1. good skin compatibility
2. low toxicity
3. high and long-lasting action
4. a high flash point of >35° C. is preferred Surprisingly, it has been found that triethyl phosphate has very good solubilities for fluorinated antiparasitics (Table 1). Triethyl phosphate has low toxicity and excellent skin compatibility with rats, dogs and cats. The flash point of 130° C. is sufficiently high for safe production. Studies with selected fluorinated antiparasitics in triethyl phosphate formulations show good and long-lasting activity against fleas and various ticks on dogs and cats.

TABLE 1

| (solubilities in % (w/w)): | | | |
|---|---|---|---|
| | triethyl phosphate | propylene carbonate | 83.3% propylene carbonate 16.7% benzyl alcohol |
| Compound 2* | 40% | 4% | 14% |
| Compound 1* | 44% | 5% | 17% |
| tigolaner** | 52% | 26% | 20% |
| pyriprole | 49% | 21% | 28% |
| fluxametamide | 20% | 3% | 6% |
| fluralaner | 41% | 7% | 13% |
| fipronil | 36% | 11% | 5% |

*definitions of Compound 1 and Compound 2: see below.
**proposed INN (see WHO Drug Information, Vol. 31, No. 2, 2017)

The aforementioned object is therefore achieved by:

A liquid formulation comprising a fluorine-containing active compound effective against parasites, and triethyl phosphate.

According to a further aspect, the invention relates to the use of the liquid formulations described herein for controlling parasites, in particular ectoparasites on animals.

DETAILED DESCRIPTION OF A PREFERRED EMBODIMENT

Antiparasitic active compounds (here also referred to as "Antiparasitics") are to be understood as meaning active compounds active against endoparasites or ectoparasites or both. For the liquid formulations described herein, preference is given to using active compounds which act against ectoparasites.

In connection with the active compounds used herein, "fluorine-containing" (or fluorinated) means in particular that the active compound in the molecule comprises, per 200 u of the molecular weight, at least one fluorine atom, preferably at least 1 fluorine atom per 160 u of the molecular weight, in particular at least 1 fluorine atom per 100 u of the molecular weight. The fluorine atoms may be attached to various radicals, e.g. to an aromatic ring. Preferably, the active compounds in the molecule comprise, per 500 u of the molecular weight, at least one trifluoromethyl group. The figures stated above, such as "per 200 u of the molecular weight" are to be understood as ranges. "At least one fluorine atom per 200 u of the molecular weight" means that molecules having a molecular weight of up to 200 u comprise one fluorine atom; correspondingly, molecules having a molecular weight of 200 to 400 u comprise at least two fluorine atoms, etc. The statements with respect to the abovementioned preferred embodiments of the fluorine-containing active compounds relating to the fluorine atoms or trifluoromethyl groups present are also to be understood accordingly.

According to one embodiment, the fluorine-containing antiparasitic active compounds have at least one 5- or 6-membered heteroaromatic ring which contains 1 to 3, preferably 1 or 2, identical or different heteroatoms selected from N, O and S, preferably from N and O.

Particular mention may be made of the following fluorine-containing antiparasitic active compounds:

Substituted benzamide compounds described in WO 2015067646 A1 or in WO 2015067647 A1, submitted at the same time:

Compounds of the general formula (I):

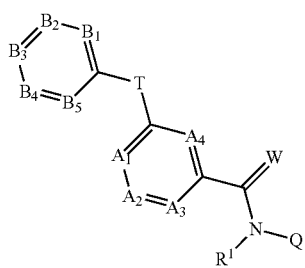

(I)

in which
$R^1$ represents H, in each case optionally substituted $C_2$-$C_6$-alkenyl, $C_2$-$C_6$-alkynyl, $C_3$-$C_7$-cycloalkyl, $C_1$-$C_6$-alkylcarbonyl, $C_1$-$C_6$-alkoxycarbonyl, aryl-($C_1$-$C_3$)-alkyl, heteroaryl-($C_1$-$C_3$)-alkyl or represents optionally substituted $C_1$-$C_6$-alkyl, preferably H or preferably $C_1$-$C_2$-alkyl, very particularly preferably H or methyl, in particular H, the moieties are as follows:
$A_1$ represents $CR^2$ or N,
$A_2$ represents $CR^3$ or N,
$A_3$ represents $CR^4$ or N,
$A_4$ represents $CR^5$ or N,
$B_1$ represents $CR^6$ or N,
$B_2$ represents $CR^7$ or N,
$B_3$ represents $CR^8$ or N,
$B_4$ represents $CR^9$ or N, and
$B_5$ represents $CR^{10}$ or N,
  but not more than three of the $A_1$ to $A_4$ moieties represent N and not more than three of the $B_1$ to $B_5$ moieties represent N;
$R^2$, $R^3$, $R^2$, $R^5$, $R^6$, $R^7$, $R^9$ and $R^{10}$ each independently of one another represent H, halogen, cyano, nitro, in each case optionally substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulfanyl, $C_1$-$C_6$-alkylsulfinyl, $C_1$-$C_6$-alkylsulfonyl, N—$C_1$-$C_6$-alkylamino, N,N-di-$C_1$-$C_6$-alkylamino or N—$C_1$-$C_3$-alkoxy-$C_1$-$C_4$-alkylamino or 1-pyrrolidinyl;
  if neither of the $A_2$ and $A_3$ moieties represents N, $R^3$ and $R^4$ together with the carbon atom to which they are bonded may form a 5- or 6-membered ring containing 0, 1 or 2 nitrogen atoms and/or 0 or 1 oxygen atom and/or 0 or 1 sulfur atom; or
  if neither of the $A_1$ and $A_2$ moieties represents N, $R^2$ and $R^3$ together with the carbon atom to which they are attached may form a 6-membered ring containing 0, 1 or 2 nitrogen atoms;

$R^8$ represents halogen, cyano, nitro, in each case optionally substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulfanyl, $C_1$-$C_6$-alkylsulfinyl, $C_1$-$C_6$-alkylsulfonyl, N—$C_1$-$C_6$-alkylamino or N,N-di-$C_1$-$C_6$-alkylamino;

W represents O or S,

Q represents H, formyl, hydroxyl, amino or in each case optionally substituted $C_1$-$C_6$-alkyl, $C_2$-$C_6$-alkenyl, $C_2$-$C_6$-alkynyl, $C_3$-$C_6$-cycloalkyl, $C_1$-$C_5$-heterocycloalkyl, $C_1$-$C_4$-alkoxy, $C_1$-$C_6$-alkyl-$C_3$-$C_6$-cycloalkyl, $C_3$-$C_6$-cycloalkyl-$C_1$-$C_6$-alkyl, $C_6$-,$C_{10}$-$C_{14}$-aryl, $C_1$-$C_5$-heteroaryl, $C_6$-,$C_{10}$-, $C_{14}$-aryl-($C_1$-$C_3$)-alkyl, $C_1$-$C_5$-heteroaryl-($C_1$-$C_3$)-alkyl, N—$C_1$-$C_4$-alkylamino, N—$C_1$-$C_4$-alkylcarbonylamino, or N,N-di-$C_1$-$C_4$-alkylamino; or represents an optionally poly-V-substituted unsaturated 6-membered carbocycle; or represents an optionally poly-V-substituted unsaturated 4-, 5- or 6-membered heterocyclic ring, where V independently of one another represents halogen, cyano, nitro, in each case optionally substituted $C_1$-$C_6$-alkyl, $C_1$-$C_4$-alkenyl, $C_1$-$C_4$-alkynyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulfanyl, $C_1$-$C_6$-alkylsulfinyl, $C_1$-$C_6$-alkylsulfonyl, or N,N-di-($C_1$-$C_6$-alkyl)amino;

T represents an optionally substituted 5-membered heteroaromatic system containing not more than 2 heteroatoms (1 or 2 heteroatoms), such as four carbon atoms and one (1) heteroatom, preferably one (1) nitrogen, one (1) oxygen or one (1) sulfur atom or three carbon atoms and two heteroatoms, preferably two nitrogen atoms, one (1) nitrogen and one (1) oxygen atom, or one (1) nitrogen and one (1) sulfur atom, and salts, N-oxides and tautomeric forms of the compounds of the formula (I).

One aspect of the present invention relates to compounds of the formula (Ia)

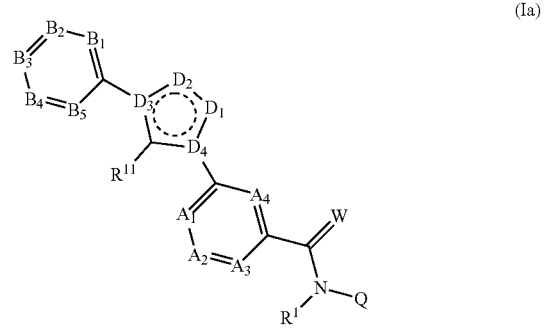

(Ia)

in which
  the $D_1$, $D_2$ moieties each independently of one another represent C—$R^{11}$ or a heteroatom selected from N and O;
  the $D_3$ and $D_4$ moieties independently of one another represent C or represent a heteroatom selected from N (in other words: the $D_3$ and $D_4$ moieties independently of one another represent C or N);
  where not more than one (1) or two moieties selected from $D_1$, $D_2$, $D_3$ and $D_4$ represent a heteroatom, where one (1) or two moieties selected from $D_1$, $D_2$, $D_3$ and $D_4$ represent a heteroatom selected from N or O in the case of $D_1$ and $D_2$, or N in the case of $D_3$ and $D_4$;

represents an aromatic system; and $R^1$, $A_1$, $A_2$, $A_3$, $A_4$, $B_1$, $B_2$, $B_3$, $B_4$, $B_5$, $R^2$, $R^3$, $R^4$, $R^5$, $R^6$, $R^7$, $R^8$, $R^9$, $R^{10}$, $R^{11}$, W, Q, V and T are defined as described herein, where not more than one moiety selected from $A_1$, $A_2$, $A_3$, $A_4$ represents N and not more than one moiety selected from $B_1$, $B_2$, $B_3$, $B_4$ and $B_5$ represents N; or where one or two moieties selected from $A_1$, $A_2$, $A_3$, $A_4$ may represent N and not more than one moieties selected from $B_1$, $B_2$, $B_3$, $B_4$ and $B_5$ represents N;

and salts, N-oxides and tautomeric forms of the compounds of the formula (I).

One embodiment of the present invention relates to compounds of the formula (Ia')

(Ia')

in which $R^1$, $R^{11}$, Q, W, $A_1$, $A_2$, $A_3$, $A_4$, $B_1$, $B_2$, $B_4$ and $B_5$ are each defined as described herein, where not more than one moiety selected from $A_1$, $A_2$, $A_3$, $A_4$ represents N and not more than one moiety selected from $B_1$, $B_2$, $B_3$, $B_4$ and $B_5$ represents N; or where one or two moieties selected from $A_1$, $A_2$, $A_3$, $A_4$ may represent N and not more than one moieties selected from $B_1$, $B_2$, $B_3$, $B_4$ and $B_5$ represents N;

$D_1$ and $D_2$ each independently of one another represent C—$R^{11}$ or a heteroatom, preferably C—$R^{11}$ or a heteroatom selected from N, O or S, more preferably C—$R^{11}$ or a heteroatom selected from N or O;

the $D_3$ and $D_4$ moieties independently of one another represent C or a heteroatom selected from N;

where not more than one (1) or two moieties selected from $D_1$, $D_2$, $D_3$ and $D_4$ represent a heteroatom, where one (1) or two moieties selected from $D_1$, $D_2$, $D_3$ and $D_4$ represent a heteroatom selected from N or O in the case of $D_1$, and $D_2$, or N in the case of $D_3$ and $D_4$;

represents an aromatic system and $R^8$ is as defined herein, preferably represents perfluorinated $C_1$-$C_4$-alkyl.

A further embodiment of the present invention relates to compounds of the formula (Ia")

(Ia")

in which $D_1$ represents C—$R^{11}$ or a heteroatom selected from N or O;
$D_2$ represents C—$R^{11}$ or a heteroatom selected from N or O;
$D_3$ represents C or N;
$D_4$ represents C or N;
$D_5$ represents C—$R^{11}$ or N;
where not more than one (1) or two moieties selected from $D_1$, $D_2$, $D_3$, $D_4$ and $D_5$ represent a heteroatom;

represents an aromatic system; and
$R^1$ represents H, in each case optionally substituted $C_2$-$C_6$-alkenyl, $C_2$-$C_6$-alkynyl, $C_3$-$C_7$-cycloalkyl, $C_1$-$C_6$-alkylcarbonyl, $C_1$-$C_6$-alkoxycarbonyl, aryl-($C_1$-$C_3$)-alkyl or heteroaryl-($C_1$-$C_3$)-alkyl or represents optionally substituted $C_1$-$C_6$-alkyl, particularly preferably H;
the moieties are as follows:
$A_1$ represents $CR^2$ or N,
$A_2$ represents $CR^3$ or N,
$A_3$ represents $CR^4$ or N,
$A_4$ represents $CR^5$ or N,
$B_1$ represents $CR^6$ or N,
$B_2$ represents $CR^7$ or N,
$B_3$ represents $CR^8$ or N,
$B_4$ represents $CR^9$ or N, and
$B_5$ represents $CR^{10}$ or N,
but not more than three of the $A_1$ to $A_4$ moieties represent N and not more than three of the $B_1$ to $B_5$ moieties simultaneously represent N;
$R^2$, $R^3$, $R^4$, $R^5$, $R^6$, $R^7$, $R^9$ and $R^{10}$ independently of one another represent H, halogen, cyano, nitro, in each case optionally substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulfanyl, $C_1$-$C_6$-alkylsulfinyl, $C_1$-$C_6$-alkylsulfonyl, N—$C_1$-$C_6$-alkylamino or N,N-di-$C_1$-$C_6$-alkylamino;
  if neither of the $A_2$ and $A_3$ moieties represents N, $R^3$ and $R^4$ together with the carbon atom to which they are attached may form a 5- or 6-membered ring containing 0, 1 or 2 nitrogen atoms and/or 0 or 1 oxygen atom and/or 0 or 1 sulfur atom, or
  if neither of the $A_1$ and $A_2$ moieties represents N, $R^2$ and $R^3$ together with the carbon atom to which they are attached may form a 6-membered ring containing 0, 1 or 2 nitrogen atoms;
$R^8$ represents halogen, cyano, nitro, in each case optionally substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulfanyl, $C_1$-$C_6$-alkylsulfinyl, $C_1$-$C_6$-alkylsulfonyl, N—$C_1$-$C_6$-alkylamino or N,N-di-$C_1$-$C_6$-alkylamino;

$R^{11}$ independently of one another represents H, halogen, cyano, nitro, amino or an optionally substituted $C_1$-$C_6$-alkyl, $C_1$-$C_6$-alkyloxy, $C_1$-$C_6$-alkylcarbonyl, $C_1$-$C_6$-alkylsulfanyl, $C_1$-$C_6$-alkylsulfinyl, $C_1$-$C_6$-alkylsulfonyl, preferably H;

W represents O or S,

Q represents H, formyl, hydroxyl, amino or in each case optionally substituted $C_1$-$C_6$-alkyl, $C_2$-$C_6$-alkenyl, $C_2$-$C_6$-alkynyl, $C_3$-$C_6$-cycloalkyl, $C_1$-$C_5$-heterocycloalkyl, $C_1$-$C_4$-alkoxy, $C_1$-$C_6$-alkyl-$C_3$-$C_6$-cycloalkyl, $C_3$-$C_6$-cycloalkyl-$C_1$-$C_6$-alkyl, $C_6$-,$C_{10}$-$C_{14}$-aryl, $C_1$-$C_5$-heteroaryl, $C_6$-,$C_{10}$-, $C_4$-aryl-($C_1$-$C_3$)-alkyl, $C_1$-$C_5$-heteroaryl-($C_1$-$C_3$)-alkyl, N—$C_1$-$C_4$-alkylamino, N—$C_1$-$C_4$-alkylcarbonylamino, or N,N-di-$C_1$-$C_4$-alkylamino; or represents an optionally poly-V-substituted unsaturated 6-membered carbocycle; or represents an optionally poly-V-substituted unsaturated 4-, 5- or 6-membered heterocyclic ring, where V independently of one another represents halogen, cyano, nitro, in each case optionally substituted $C_1$-$C_6$-alkyl, $C_1$-$C_4$-alkenyl, $C_1$-$C_4$-alkynyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulfanyl, $C_1$-$C_6$-alkylsulfinyl, $C_1$-$C_6$-alkylsulfonyl, or N,N-di-($C_1$-$C_6$-alkyl)amino;

and salts, N-oxides and tautomeric forms of the compounds of the formula (Ia").

A further embodiment of the present invention relates to compounds of the formula (Ia"), where the compounds of the formula (Ia") are compounds of the formula (I-T3)

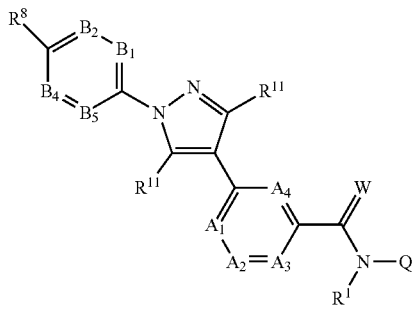

(I-T3)

in which $R^1$, $A_1$, $A_2$, $A_3$, $A_4$, $R^{11}$, $B_1$, $B_2$, $B_4$, $B_5$, $R^8$, Q and W are each defined as described herein, where not more than one moiety selected from $A_1$, $A_2$, $A_3$, $A_4$ represents N and not more than one moiety selected from $B_1$, $B_2$, $B_3$, $B_4$ and $B_5$ represents N; or where one or two moieties selected from $A_1$, $A_2$, $A_3$, $A_4$ may represent N and not more than one moiety selected from $B_1$, $B_2$, $B_3$, $B_4$ and $B_5$ represents N.

A further embodiment of the present invention relates to compounds of the formula (Ia"), where the compounds of the formula (Ia") are compounds of the formula (I-T2)

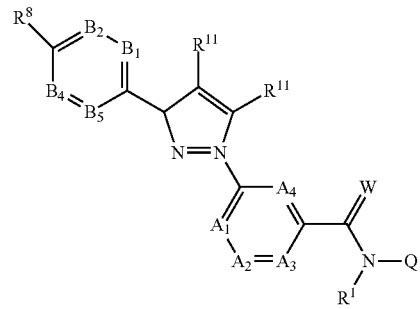

(I-T2)

in which $R^1$, $A_1$, $A_2$, $A_3$, $A_4$, $R^{11}$, $B_1$, $B_2$, $B_4$, $B_5$, $R^8$, Q and W are each defined as described herein, where not more than one moiety selected from $A_1$, $A_2$, $A_3$, $A_4$ represents N and not more than one moiety selected from $B_1$, $B_2$, $B_3$, $B_4$ and $B_5$ represents N; or where one or two moieties selected from $A_1$, $A_2$, $A_3$, $A_4$ may represent N and not more than one moiety selected from $B_1$, $B_2$, $B_3$, $B_4$ and $B_5$ represents N.

A further embodiment of the present invention relates to compounds of the formula (Ia"), where the compounds of the formula (Ia") are compounds of the formula (I-T4)

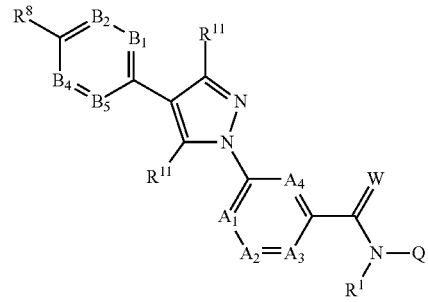

(I-T4)

in which $R^1$, $A_1$, $A_2$, $A_3$, $A_4$, $R^{11}$, $B_1$, $B_2$, $B_4$, $B_5$, $R^8$, Q and W are each defined as described herein, where not more than one moiety selected from $A_1$, $A_2$, $A_3$, $A_4$ represents N and not more than one moiety selected from $B_1$, $B_2$, $B_3$, $B_4$ and $B_5$ represents N; or where one or two moieties selected from $A_1$, $A_2$, $A_3$, $A_4$ may represent N and not more than one moiety selected from $B_1$, $B_2$, $B_3$, $B_4$ and $B_5$ represents N.

A further embodiment of the present invention relates to compounds of the formula (Ia"), where the compounds of the formula (Ia") are compounds of the formula (I-T22)

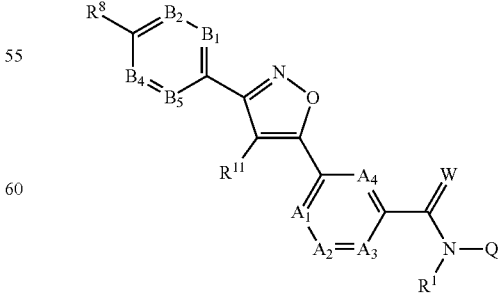

(I-T-22)

in which $R^1$, $A_1$, $A_2$, $A_3$, $A_4$, $R^{11}$, $B_1$, $B_2$, $B_4$, $B_5$, $R^8$, Q and W are each defined as described herein, where not more than one moiety selected from $A_1$, $A_2$, $A_3$, $A_4$ represents N and not more than one moiety selected from $B_1$, $B_2$, $B_3$, $B_4$ and $B_5$ represents N; or where one or two moieties selected from $A_1$, $A_2$, $A_3$, $A_4$ may represent N and not more than one moiety selected from $B_1$, $B_2$, $B_3$, $B_4$ and $B_5$ represents N.

A further embodiment of the present invention relates to compounds of the formula (Ia″), where the compounds of the formula (Ia″) are compounds of the formula (I-T23)

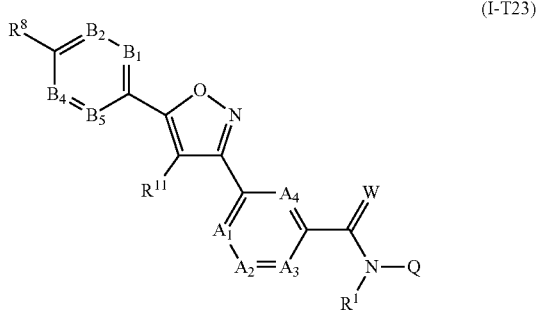

(I-T23)

in which $R^1$, $A_1$, $A_2$, $A_3$, $A_4$, $R^{11}$, $B_1$, $B_2$, $B_4$, $B_5$, $R^8$, Q and W are each defined as described herein, where not more than one moiety selected from $A_1$, $A_2$, $A_3$, $A_4$ represents N and not more than one moiety selected from $B_1$, $B_2$, $B_3$, $B_4$ and $B_5$ represents N; or where one or two moieties selected from $A_1$, $A_2$, $A_3$, $A_4$ may represent N and not more than one moiety selected from $B_1$, $B_2$, $B_3$, $B_4$ and $B_5$ represents N.

A further embodiment of the present invention relates to compounds of the formulae and embodiments described herein, where $R^{11}$ represents H and W represents O.

A further embodiment of the present invention relates to compounds of the formulae and embodiments described herein, where $R^{11}$ represents H and W represents O and $B_3$ represents C—$R^8$, $R^8$ represents halogen-substituted $C_1$-$C_3$-alkyl (preferably perhalogenated $C_1$-$C_3$-alkyl, more preferably perfluorinated $C_1$-$C_3$-alkyl) or halogen-substituted $C_1$-$C_3$-alkoxy (preferably perhalogenated $C_1$-$C_3$-alkoxy, more preferably perfluorinated $C_1$-$C_3$-alkoxy). A further embodiment of the present invention relates to compounds of the formulae and embodiments described herein, where the $A_1$ to $A_4$ and $B_1$ to $B_5$ moieties are as follows:
$A_1$ represents C—H,
$A_2$ represents $CR^3$ or N,
$A_3$ represents $CR^4$,
$A_4$ represents C—H,
$B_1$ represents $CR^6$ or N,
$B_2$ represents C—H,
$B_3$ represents $CR^8$,
$B_4$ represents C—H and
$B_5$ represents $CR^{10}$ or N.

A further embodiment of the present invention relates to compounds of the formulae and embodiments described herein, where $R^1$ represents H.

A further embodiment of the present invention relates to compounds of the formulae and embodiments described herein, where Q represents fluorine-substituted $C_1$-$C_4$-alkyl, $C_3$-$C_4$-cycloalkyl, optionally cyano- or fluorine-substituted $C_3$-$C_4$-cycloalkyl, $C_4$-$C_6$-heterocycloalkyl, 1-oxidothietan-3-yl, 1,1-dioxidothietan-3-yl, benzyl, pyridin-2-ylmethyl, methylsulfonyl or 2-oxo-2-(2,2,2-trifluoroethylamino)ethyl.

A further embodiment of the present invention relates to compounds of the formulae and embodiments described herein, where $R^8$ represents halogen or halogen-substituted $C_1$-$C_4$-alkyl.

Yet a further embodiment of the present invention relates to compounds of the formulae described herein, where $R^{11}$ represents H.

Yet a further embodiment of the present invention relates to compounds of the formulae described herein, where $R^6$, $R^7$, $R^9$ and $R^{10}$ independently of one another represent H, halogen, cyano, nitro, in each case optionally substituted $C_1$-$C_4$-alkyl, $C_3$-$C_4$-cycloalkyl, $C_1$-$C_4$-alkoxy, N-alkoxyiminoalkyl, $C_1$-$C_4$-alkylsulfanyl, $C_1$-$C_4$-alkylsulfinyl, $C_1$-$C_4$-alkylsulfonyl, N—$C_1$-$C_4$-alkylamino, N,N-di-$C_1$-$C_4$-alkylamino.

Yet a further embodiment of the present invention relates to compounds of the formulae described herein, where $R^2$, $R^3$, $R^4$ and $R^5$ independently of one another represent H, halogen, cyano, nitro, in each case optionally substituted $C_1$-$C_4$-alkyl, $C_3$-$C_4$-cycloalkyl, $C_1$-$C_4$-alkoxy, N—$C_1$-$C_4$-alkoxyimino-$C_1$-$C_4$-alkyl, $C_1$-$C_4$-alkylsulfanyl, $C_1$-$C_4$-alkylsulfinyl, $C_1$-$C_4$-alkylsulfonyl, N—$C_1$-$C_4$-alkylamino or N,N-di-$C_1$-$C_4$-alkylamino.

Yet a further embodiment of the present invention relates to compounds of the formulae described herein, where the $A_1$ to $A_4$ and $B_1$ to $B_5$ moieties are as follows:
$A_1$ represents C—H,
$A_2$ represents $CR^3$ or N,
$A_3$ represents $CR^4$,
$A_4$ represents C—H,
$B_1$ represents $CR^6$ or N,
$B_2$ represents C—H,
$B_3$ represents $CR^8$,
$B_4$ represents C—H and
$B_5$ represents $CR^{10}$ or N.

Yet a further embodiment of the present invention relates to compounds of the formulae described herein, where $R^1$ represents H.

Yet a further embodiment of the present invention relates to compounds of the formulae described herein, where $R^1$ represents methyl.

Yet a further embodiment of the present invention relates to compounds of the formulae described herein, where Q represents fluorine-substituted or carbonamide (—C(=O)N(R)$_2$, where R independently of one another represents H, $C_1$-$C_3$-alkyl or halogen-substituted $C_1$-$C_3$-alkyl)-substituted $C_1$-$C_4$-alkyl, optionally cyano- or fluorine-substituted $C_3$-$C_4$-cycloalkyl, $C_4$-$C_6$-heterocycloalkyl, 1-oxidothietan-3-yl, 1,1-dioxidothietan-3-yl, benzyl, pyridin-2-ylmethyl, methylsulfonyl or 2-oxo-2-(2,2,2-trifluoroethylamino)ethyl.

Yet a further embodiment of the present invention relates to compounds of the formulae described herein, where Q represents 2,2,2-trifluoroethyl, 2,2-difluoroethyl, 3,3,3-trifluoropropyl, cyclopropyl, cyclobutyl, 1-cyanocyclopropyl, trans-2-fluorocyclopropyl, or cis-2-fluorocyclopropyl, oxetan-3-yl, thietan-3-yl, 1-oxidothietan-3-yl, 1,1-dioxidothietan-3-yl, benzyl, pyridin-2-ylmethyl, methylsulfonyl or 2-oxo-2-(2,2,2-trifluoroethylamino)ethyl.

Yet a further embodiment of the present invention relates to compounds of the formulae described herein, where $R^8$ represents halogen or halogen-substituted $C_1$-$C_4$-alkyl.

The following preferred examples may be mentioned:
2-chloro-N-cyclopropyl-5-[1-[4-(1,1,1,2,3,3,3-heptafluoropropan-2-yl)-2-methyl-6-(trifluoromethyl)phenyl]-1H-pyrazol-4-yl]benzamide:

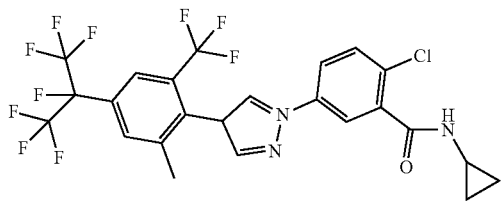

2-chloro-N-(1-cyanocyclopropyl)-5-[1-[4-(1,1,1,2,3,3,3-heptafluoropropan-2-yl)-2-methyl-6-(trifluoromethyl)phenyl]-1H-pyrazol-4-yl]benzamide:

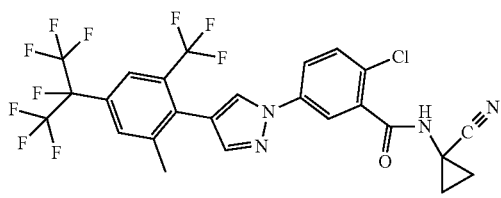 [SMILES: Cc1cc(C(F)(C(F)(F)F)C(F)(F)F)cc(C(F)(F)F)c1-c1cnn(-c2ccc(Cl)c(C(=O)NC3(C#N)CC3)c2)c1]

2-chloro-N-cyclopropyl-5-[4-[2,6-dimethyl-4-[1,2,2,2-tetrafluoro-1-(trifluoromethyl)ethyl]phenyl]pyrazol-1-yl]benzamide:

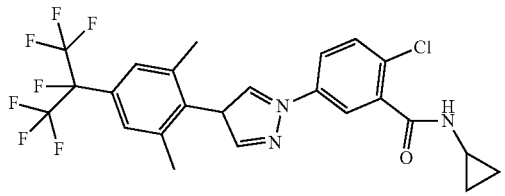

2-chloro-N-(1-cyanocyclopropyl)-5-[4-[2,6-dichloro-4-[1,2,2,2-tetrafluoro-1-(trifluoromethyl)ethyl]phenyl]pyrazol-1-yl]benzamide:

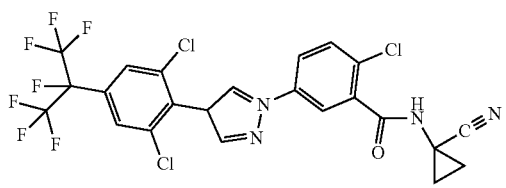

2-chloro-5-[3-[2-chloro-4-[1,2,2,2-tetrafluoro-1-(trifluoromethyl)ethyl]-6-(trifluoromethyl)phenyl]isoxazol-5-yl]-N-cyclopropylbenzamide:

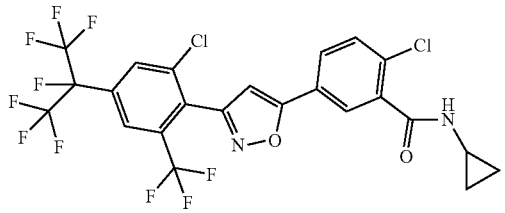 [SMILES: O=C(NC1CC1)c1cc(-c2cc(-c3c(Cl)cc(C(F)(C(F)(F)F)C(F)(F)F)cc3C(F)(F)F)no2)ccc1Cl]

2-chloro-N-(1-cyanocyclopropyl)-5-[3-[2-methyl-4-[1,2,2,2-tetrafluoro-1-(trifluoromethyl)ethyl]-6-(trifluoromethyl)phenyl]isoxazol-5-yl]benzamide:

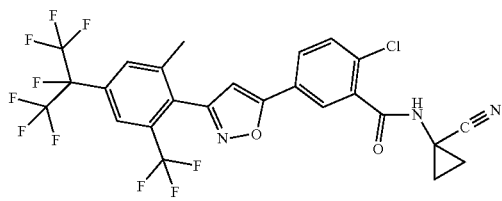 [SMILES: Cc1cc(C(F)(C(F)(F)F)C(F)(F)F)cc(C(F)(F)F)c1-c1cc(-c2ccc(Cl)c(C(=O)NC3(C#N)CC3)c2)on1]

2-chloro-N-(1-cyanocyclopropyl)-5-[1-[2,6-dichloro-4-[1,2,2,2-tetrafluoro-1-(trifluoromethyl)ethyl]phenyl]pyrrol-3-yl]benzamide:

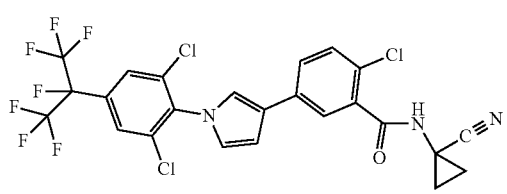 [SMILES: N#CC1(NC(=O)c2cc(-c3ccn(-c4c(Cl)cc(C(F)(C(F)(F)F)C(F)(F)F)cc4Cl)c3)ccc2Cl)CC1]

2-chloro-5-[3-[2-chloro-4-[1,2,2,2-tetrafluoro-1-(trifluoromethyl)ethyl]-6-(trifluoromethyl)phenyl]pyrrol-1-yl]-N-cyclopropylbenzamide:

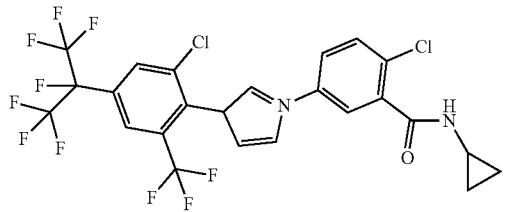

2-chloro-5-[1-[2-chloro-4-[1,2,2,2-tetrafluoro-1-(trifluoromethyl)ethyl]-6-(trifluoromethoxy)phenyl]-1H-pyrazol-4-yl]-N-cyclopropyl-3-pyridinecarboxamide (Compound 1):

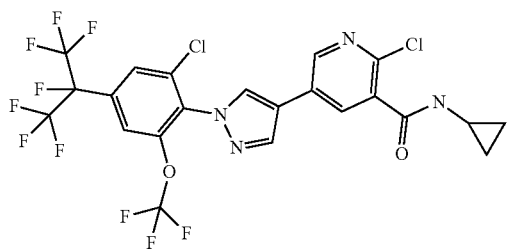 [SMILES: O=C(NC1CC1)c1cc(-c2cnn(-c3c(Cl)cc(C(F)(C(F)(F)F)C(F)(F)F)cc3OC(F)(F)F)c2)cnc1Cl]

2-chloro-5-[1-[2-chloro-4-[1,2,2,2-tetrafluoro-1-(trifluoromethyl)ethyl]-6-(trifluoromethyl)phenyl]-1H-pyrazol-4-yl]-N-cyclopropyl-3-pyridinecarboxamide (Compound 2):

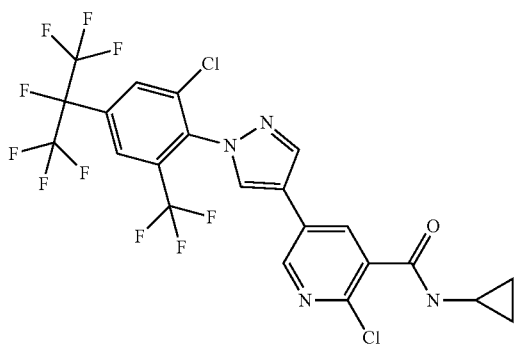 [SMILES: O=C(NC1CC1)c1cc(-c2cnn(-c3c(Cl)cc(C(F)(C(F)(F)F)C(F)(F)F)cc3C(F)(F)F)c2)cnc1Cl]

Other antiparasitic active compounds which may be mentioned are: The compound having the proposed INN tigolaner (see also WO2014/122083):

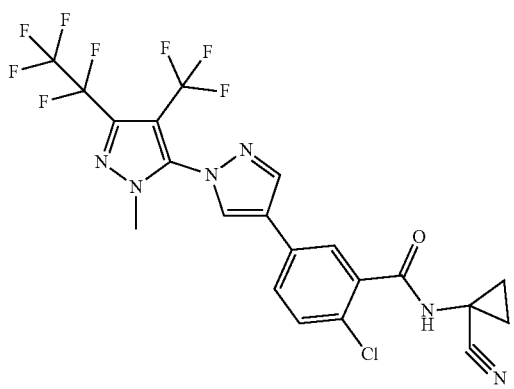 [SMILES: Cn1nc(C(F)(F)C(F)(F)F)c(C(F)(F)F)c1-n1cc(-c2ccc(Cl)c(C(=O)NC3(C#N)CC3)c2)cn1]

Other antiparasitic active compounds are compounds from the class of the arylisoxazolines, preferred examples which may be mentioned being: fluralaner (WO2005085216), afoxolaner (WO2009126668), sarolaner (WO 2012120399), lotilaner (WO2010070068) or fluxametamide. Other antiparasitic active compounds are compounds from the class of the arylpyrazoles, in particular pyriprole or fipronil. The formulation of the invention is preferably a solution.

The active compound content of the formulation depends on the active compound in question and is set such that good efficacy is achieved together with good compatibility. Usually, the active compound content is from 1 to 60% (w/w), preferably 10 to 50% (w/w), particularly preferably 20 to 40% (w/w). According to a further embodiment, in the case of highly effective active compounds, the content may be from 1 to 30% (w/w), preferably 1 to 20% (w/w), particularly preferably 5 to 10% (w/w).

The formulation usually comprises at least 10% (w/w), preferably at least 30% (w/w), particularly preferably at least 50% by weight, very particularly preferably at least 60% by weight of triethyl phosphate. Correspondingly, the amounts of triethyl phosphate are usually from 10 to 95% (w/w), preferably 15 to 90% (w/w), particularly preferably 50 to 80% (w/w). If solvent mixtures are employed (suitable cosolvents: see below), in accordance with a further embodiment the content of triethyl phosphate may also be lower, e.g. from 5 to 50% (w/w), preferably 10 to 40% (w/w), particularly preferably 15 to 35% (w/w).

According to one embodiment, the formulation comprises triethyl phosphate as only solvent.

In other use forms, in addition to triethyl phosphate, at least one further cosolvent suitable for veterinary use is present. The cosolvent should be miscible with triethyl phosphate in the chosen amount and should have no adverse effect on skin compatibility and toxicity. Preferably, it should not reduce the solubility and improve the cosmetic properties.

The following may be mentioned as preferred cosolvents: 1-methoxy-2-propyl acetate, 2-methoxy-1,3-dioxolane, 1-methoxy-2-butanol, 3,4-hexanedione, 2-heptanone, 2,3-pentadione, 3-hexanone, acetone, laurocapram, ethyl acetate, 1-dodecyl-2-pyrrolidinone, 2-pentanone, 3-pentanone, 3-methyl-2-butanone, cyclohexanone, propylene glycol, polyethylene glycol, triacetine, limonene, medium-chain triglycerides, ethyl oleate, triethyl citrate, ethylene glycol, 6-methyl-2,4-heptanedione, 2-methoxy-1-propanol, tert-butanol, 1-butanol, tetraglycol, isopropanol, 2-amino-6-methylheptane, isosorbide dimethyl ether, diethylene glycol monoethyl ether, solketal, diethyl carbonate, 3,5-heptanedione, 2,3-heptanedione, ethanol, 2-phenoxyethanol, diethyl phthalate, tributyl 2-acetylcitrate, 2,6-dimethylpyridine, tris-(2-ethylhexyl) phosphate, 4-methyl-2-pentanone, propylene glycol monoethyl ether acetate, octyldodecanol, 6-methyl-3,5-heptanedien-2-one. The following may be mentioned as particularly preferred cosolvents: 2-butanone, 2-pyrrolidone, 4-methylpent-3-en-2-one, epsilon-caprolactone, gamma-hexalactone, 1-methoxy-2-propanol, dimethyl sulfoxide, N,N-diethyl-m-toluamide, benzyl alcohol, propylene carbonate, isosorbide dimethyl ether, 2-heptanone, N-methylcaprolactam, gamma-butyrolactone, 1-octyl-2-pyrrolidone.

It is possible to employ individual cosolvents or else two or more cosolvents in combination in the formulations according to the invention.

Usually, the proportion of cosolvent or cosolvent mixture is from 1 to 85% w/w, preferably 20 to 80% w/w, particularly preferably 30 to 75% w/w. According to one embodiment, the proportion of cosolvent is higher than that of triethyl phosphate; in this case, the proportion of cosolvent is usually from 40 to 85% w/w, preferably 50 to 80% (w/w), particularly preferably 60 to 80% (w/w).

According to a further embodiment, the proportion of cosolvent is lower than that of triethyl phosphate; in this case, the proportion of cosolvent is usually from 1 to 40% w/w, preferably 5 to 35% (w/w), particularly preferably 10 to 30% (w/w).

The formulations described may also comprise combinations of active compounds to improve the activity by synergisms or to widen the activity spectrum.

The formulations may optionally contain further pharmaceutically acceptable auxiliaries and additives, for example surfactants, antioxidants and penetrants.

Suitable surfactants are, for example, polysorbates (Tween®), sorbitan ester (Span®), polyoxyethylene stearate (Myrj®, Brij®, Cremophor), glycerol mono- or distearate, poloxamers (Pluronic F68), oleoyl macrogol-6 glycerides (Labrafil®) and others. Surfactants are usually employed in concentrations of up to 5% (w/w), in particular from 0.5 to 5% (w/w).

Suitable antioxidants are, for example, butylated hydroxytoluene (BHT), butylated hydroxyanisole (BHA), vitamin E and others, which can be employed in concentrations of up to 4% (w/w), in particular 0.5 to 4% (w/w).

Penetrants can be employed, for example, if the penetration of the active compound(s) into or through the skin is desired and to be improved. Penetrants are, for example, alcohols (e.g. ethanol, isopropanol, benzyl alcohol, isostearyl alcohol, inter alia), azacycloalkanones (e.g. laurocapram, inter alia), dioxolanes (e.g. 2-nonyl-1,3-dioxolane), fatty acids and derivatives (e.g. lauric acid, oleic acid, heptanoic acid, palmitic acid, linoleic acid, isopropyl myristate), esters (e.g. methyl, ethyl, butyl acetate, methyl valerate and palminitate, longer-chain fatty acid esters from isopropyl myristate (C17) to isocetyl stearate (C34)], urea and urea derivatives, pyrrolidones (e.g. 2-pyrrolidone, N-methyl-2-pyrrolidone, N-(2-hydroxyethyl)-2-pyrrolidone, 2-pyrrolidone-5-carboxylic acid), sulfoxides (e.g. dimethyl sulfoxide), terpenes (e.g. limonene, 1,8-cineol, nerolidol), glycol ether (e.g. diethylene glycol monoethyl ether [Transcutol]). Penetrants can be employed in concentrations of from 1 to 60% (w/w), e.g. 1 to 30% (w/w), 1 to 20% (w/w), 10 to 50% (w/w), 20 to 40% (w/w) or 40 to 60% (w/w).

For the preparation, the active compound or the active compounds is/are dissolved in the solvent or the solvent mixture at room temperature or at elevated temperature. If the formulation comprises different solvents, the active compound or the active compounds can initially be dissolved in one solvent or in a partial mixture of the different solvents, preferably the solvent/solvent mixture having the best dissolution properties.

The formulations described herein are intended for use against parasites in/on animals, in particular ectoparasites or endoparasites. The term "endoparasite" includes in particular helminths and protozoa, such as coccidia. Ectoparasites are typically and preferably arthropods, in particular insects or acarids. Naturally, the activity spectrum of the formulations depends on the active compound or active compound mixture present.

In principle, the formulations according to the invention are suitable for the control of parasites encountered in animal breeding and animal husbandry in livestock, breeding, zoo, laboratory, experimental and domestic animals. They are active against all or specific stages of development of the parasites.

Agricultural livestock include, for example, mammals, such as sheep, goats, horses, donkeys, camels, buffalo, rabbits, reindeer, fallow deer and especially cattle and pigs; or poultry such as turkeys, ducks, geese and in particular chickens.

Domestic animals include, for example, mammals, such as hamsters, guinea pigs, rats, mice, chinchillas, ferrets, and in particular dogs, cats, caged birds; reptiles, amphibians or aquarium fish.

In a specific embodiment, the compounds of the formula (I) are administered to mammals.

In another specific embodiment, the compounds of the formula (I) are administered to birds, namely caged birds or particularly poultry.

According to one embodiment, the formulations according to the invention are suitable for use in pets, in particular mammals, preferably dogs or cats.

Use of the compounds of the formula (I) for the control of animal parasites is intended to reduce or prevent illness, cases of death and reductions in performance (in the case of meat, milk, wool, hides, eggs and the like), such that more economical and simpler animal keeping is enabled and better animal well-being is achievable.

In relation to the field of animal health, the term "control" or "controlling" in the present context means that, by employing the formulations according to the invention, the incidence of the particular parasite in an animal infected with such parasites can be reduced to an innocuous degree. More specifically, "controlling" in the present context means that the compounds of the formula (I) kill the respective parasite, inhibit its growth, or inhibit its proliferation.

The formulations according to the invention are intended for topical administration, where topical is to be understood as an external application of the formulations to the skin of the animal to be treated—i.e. dermal. Examples include:

The spot-on application comprises the application of relatively small amounts of the formulation (e.g. 0.1 to 20 ml, preferably 0.2 to 10 ml, in particular 0.3 to 5 ml) to limited skin areas, usually to the neck or back of the animal.

The pour-on application is similar to the spot-on application. However, larger amounts of the formulation are applied (e.g. 5 to 100 ml, in particular 8 to 50 ml).

Here, the active compound may act systemically, i.e. an effective amount of the active compound penetrates the skin and is distributed in the animal by the circulatory system.

Non-systemic action is also feasible: only insubstantial amounts of the active compound penetrate the skin, if any. Instead, the active compound spreads on the surface of the animal, where it unfolds its action. Obviously, non-systemic administration is unsuitable for formulations against endoparasites.

EXAMPLES

Example 1

| | |
|---|---|
| 2-chloro-5-[1-[2-chloro-4-[1,2,2,2-tetrafluoro-1-(trifluoromethyl)ethyl]-6-(methoxy) phenyl]-1H-pyrazol-4-yl]-N-cyclopropyl-3-pyridinecarboxamide (Compound 1) | 30.0 g |
| triethyl phosphate | 87.1 g |
| | 117.1 g = 100 ml |

Example 2

| | |
|---|---|
| Compound 1 | 30.0 g |
| 1-methoxy-2-propanol | 47.4 g |
| DMSO | 15.8 g |
| triethyl phosphate | 15.8 g |
| | 109.0 g = 100 ml |

Example 3

| | |
|---|---|
| 2-chloro-5-[1-[2-chloro-4-[1,2,2,2-tetrafluoro-1-(trifluoromethyl)ethyl]-6-(trifluoromethyl)phenyl]-1H-pyrazol-4-yl]-N-cyclopropyl-3-pyridinecarboxamide (Compound 2) | 30.0 g |
| triethyl phosphate | 85.6 g |
| | 115.6 g = 100 ml |

Example 4

| | |
|---|---|
| fipronil | 30.0 g |
| triethyl phosphate | 70.0 g |
| | 100.0 g |

Example 5

| | |
|---|---|
| fluralaner | 30.0 g |
| triethyl phosphate | 70.0 g |
| | 100.0 g |

Biological Example In-Vivo Efficacy Data (Cats, Dogs)

To test the efficacy of substances acting on ectoparasites, cats and dogs are experimentally populated (infested) with fleas and ticks. In the efficacy evaluation, the data of the treated animals are compared to the data of untreated control animals.

Per infestation, 40-50 ticks and about 100 fleas are applied to each individual animal.

The treatment day is counted as Day 0; correspondingly, the first week is counted as Week 0 (Days 0-6). Accordingly, Week 1 corresponds to Days 7-13 and Week 8 to Days 56-62 after treatment.

Fleas are left on the dog or cat for 24 or 48 (±4 h) hours. After this time, the fleas are removed from the animal using a flea comb. The fleas removed by combing are collected and counted. When counting the fleas, the fleas are categorized into live and dead fleas. For the parasite count, only the live fleas are taken into consideration.

Ticks are left on the dog or cat for 48 (±4 h) hours. After this time, the ticks are manually removed from the animal, optionally using a pair of tweezers. The removed ticks are collected and counted. When counting the ticks, the ticks are categorized into free live ticks, attached live ticks, free dead ticks and attached dead ticks. For the parasite count, only the attached live ticks are taken into consideration.

The efficacy against the parasite in question is calculated using the formula below:

% efficacy=$(N2-N1)/N2 \times 100$.

N1=geometric mean of the parasite count in the treated group (parasite count: live fleas or live attached ticks)
N2=geometric mean of the parasite count in the untreated group. (parasite count: live fleas or live attached ticks)

In animal experiments with dogs and cats at a dosage of 0.1 ml per kg of body weight (30% w/v solution, corresponds to 30 mg per kg), the examples in the table below showed an efficacy of at least 8 weeks against fleas (*Ctenocephalides*) and ticks (*Dermacentor, Rhipicephalus* and *Ixodes*). For details, see Table 2 below:

TABLE 2

| | | Data for efficacy against ectoparasites | | | |
|---|---|---|---|---|---|
| Animal species | Formulation | fleas | *Ixodes ricinus* | *Rhipicephalus saguineus* | *Dermacentor variabilis* |
| dog | Example 3 | 9 weeks (100%) count 24 (±4) h | 9 weeks (100%) count 48 h (±4) h | 9 weeks (100%) count 48 h (±4) h | 8 weeks (92%) count 48 h (±4) h |

TABLE 2-continued

| | | Data for efficacy against ectoparasites | | | |
|---|---|---|---|---|---|
| Animal species | Formulation | fleas | *Ixodes ricinus* | *Rhipicephalus saguineus* | *Dermacentor variabilis* |
| dog | Example 1 | 8 weeks (100%) count 24 (±4) h | 10 weeks (100%) count 48 h (±4) h | 10 weeks (99%) count 48 h (±4) h | 8 weeks (100%) count 48 h (±4 )h |
| dog | Example 2 | 8 weeks (100%) count 24 (±4) h | 10 weeks (100%) count 48 h (±4) h | 10 weeks (100%) count 48 h (±4) h | 8 weeks (100%) count 48 h (±4) h |
| cat | Example 1 | 8 weeks (100%) count 24 (±4) h | 8 weeks (100%) count 48 h (±4) h | not examined | not examined |

The invention claimed is:

1. A liquid formulation, comprising a fluorine-containing antiparasitic active compound and triethyl phosphate, wherein the liquid composition is a homogenous solution.

2. The liquid formulation according to claim 1, wherein the fluorine-containing active compound comprises at least one fluorine atom per 200 u of the molecular weight.

3. The liquid formulation according to claim 1, wherein the fluorine-containing active compound comprises at least one trifluoromethyl group per 500 u of the molecular weight.

4. The liquid formulation according to claim 1, wherein the fluorine-containing active compound is a compound of formula (I):

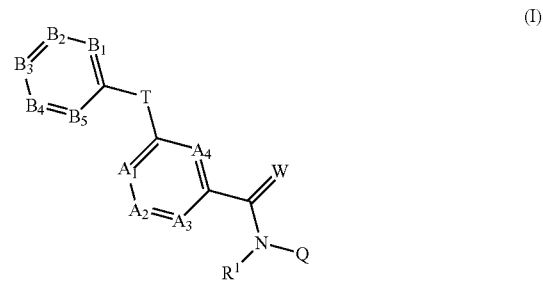

(I)

in which
$R^1$ represents H, optionally substituted $C_2$-$C_6$-alkenyl, $C_2$-$C_6$-alkynyl, $C_3$-$C_7$-cycloalkyl, $C_1$-$C_6$-alkylcarbonyl, $C_1$-$C_6$-alkoxycarbonyl, aryl-($C_1$-$C_3$)-alkyl, or heteroaryl-($C_1$-$C_3$)-alkyl,
$A_1$ represents $CR^2$ or N,
$A_2$ represents $CR^3$ or N,
$A_3$ represents $CR^4$ or N,
$A_4$ represents $CR^5$ or N,
$B_1$ represents $CR^6$ or N,
$B_2$ represents $CR^7$ or N,
$B_3$ represents $CR^8$ or N,
$B_4$ represents $CR^9$ or N, and
$B_5$ represents $CR^{10}$ or N,
wherein not more than three of the $A_1$ to $A_4$ moieties represent N and not more than three of the $B_1$ to $B_5$ moieties represent N;
$R^2$, $R^3$, $R^4$, $R^5$, $R^6$, $R^7$, $R^9$ and $R^{10}$ each independently of one another represent H, halogen, cyano, nitro, in each case optionally substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulfanyl, $C_1$-$C_6$-alkylsulfinyl, $C_1$-$C_6$- alkylsulfonyl, N—$C_1$-$C_6$-alkylamino, N,N-di-$C_1$-$C_6$-alkylamino or N—$C_1$-$C_3$-alkoxy-$C_1$-$C_4$-alkylamino or 1-pyrrolidinyl;

wherein if neither of the $A_2$ and $A_3$ moieties represents N, $R^3$ and $R^4$ together with the carbon atom to which they are bonded may form a 5- or 6-membered ring containing 0, 1 or 2 nitrogen atoms and/or 0 or 1 oxygen atom and/or 0 or 1 sulfur atom; or wherein if neither of the $A_1$ and $A_2$ moieties is N, $R^2$ and $R^3$ together with the carbon atom to which they are attached may form a 6-membered ring containing 0, 1 or 2 nitrogen atoms;

$R^8$ represents halogen, cyano, nitro, each optionally substituted with $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulfanyl, $C_1$-$C_6$-alkylsulfinyl, $C_1$-$C_6$-alkylsulfonyl, N—$C_1$-$C_6$-alkylamino or N,N-di-$C_1$-$C_6$-alkylamino;

W represents O or S,

Q represents H, formyl, hydroxyl, amino, each optionally substituted with $C_1$-$C_6$-alkyl, $C_2$-$C_6$-alkenyl, $C_2$-$C_6$-alkynyl, $C_3$-$C_6$-cycloalkyl, $C_1$-$C_5$-heterocycloalkyl, $C_1$-$C_4$-alkoxy, $C_1$-$C_6$-alkyl-$C_3$-$C_6$-cycloalkyl, $C_3$-$C_6$-cycloalkyl-$C_1$-$C_6$-alkyl, $C_6$-,$C_{10}$-$C_{14}$-aryl, $C_1$-$C_5$-heteroaryl, $C_6$-,$C_{10}$-,$C_{14}$-aryl-($C_1$-$C_3$)-alkyl, $C_1$-$C_5$-heteroaryl-($C_1$-$C_3$)-alkyl, N—$C_1$-$C_4$-alkylamino, N—$C_1$-$C_4$-alkylcarbonylamino, or N,N-di-$C_1$-$C_4$-alkylamino; or represents an optionally poly-V-substituted unsaturated 6-membered carbocycle; or represents an optionally poly-V-substituted unsaturated 4-, 5- or 6-membered heterocyclic ring, where V independently of one another represents halogen, cyano, nitro, each optionally substituted with $C_1$-$C_6$-alkyl, $C_1$-$C_4$-alkenyl, $C_1$-$C_4$-alkynyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulfanyl, $C_1$-$C_6$-alkylsulfinyl, $C_1$-$C_6$-alkylsulfonyl, or N,N-di-($C_1$-$C_6$-alkyl)amino;

T represents an optionally substituted 5-membered heteroaromatic system containing not more than 2 heteroatoms (1 or 2 heteroatoms), optionally four carbon atoms and one (1) heteroatom, optionally one (1) nitrogen, one (1) oxygen or one (1) sulfur atom or three carbon atoms and two heteroatoms, optionally two nitrogen atoms, one (1) nitrogen and one (1) oxygen atom, or one (1) nitrogen and one (1) sulfur atom, provided that the compound of formula (I) comprises at least one fluorine atom per 200 u of the molecular weight;

or a salt, N-oxide or tautomeric form of a compound of formula (I).

5. The liquid formulation according to claim 1, where the fluorine-containing active compound is selected from the group consisting of: 2-chloro-N-cyclopropyl-5-[1-[4-(1,1,1,2,3,3,3-heptafluoropropan-2-yl)-2-methyl-6-(trifluoromethyl)phenyl]-1H-pyrazol-4-yl]benzamide, 2-chloro-N-(1-cyanocyclopropyl-5-[1-[4-(1,1,1,2,3,3,3-heptafluoropropan-2-yl)-2-methyl-6-(trifluoromethyl)phenyl]-1H-pyrazol-4-yl]benzamide, 2-chloro-N-cyclopropyl-5-[4-[2,6-dimethyl-4-[1,2,2,2-tetrafluoro-1-(trifluoromethyl)ethyl]phenyl]pyrazol-1-yl]benzamide, 2-chloro-N-(1-cyanocyclopropyl)-5-[4-[2,6-dichloro-4-[1,2,2,2-tetrafluoro-1-(trifluoromethyl)ethyl]phenyl]pyrazol-1-yl]benzamide, 2-chloro-5-[3-[2-chloro-4-[1,2,2,2-tetrafluoro-1-(trifluoromethyl)ethyl]-6-(trifluoromethyl)phenyl]isoxazol-5-yl]-N-cyclopropylbenzamide, 2-chloro-N-(1-cyanocyclopropyl)-5-[3-[2-methyl-4-[1,2,2,2-tetrafluoro-1-(trifluoromethyl)ethyl]-6-(trifluoromethyl)phenyl]isoxazol-5-yl]benzamide, 2-chloro-N-(1-cyanocyclopropyl)-5-[1-[2,6-dichloro-4-[1,2,2,2-tetrafluoro-1-(trifluoromethyl)ethyl]phenyl]pyrrol-3-yl]benzamide, 2-chloro-5-[3-[2-chloro-4-[1,2,2,2-tetrafluoro-1-(trifluoromethyl)ethyl]-6-(trifluoromethyl)phenyl]pyrrol-1-yl]-N-cyclopropylbenzamide, 2-chloro-5-[1-[2-chloro-4-[1,2,2,2-tetrafluoro-1-(trifluoromethyl)ethyl]-6-(trifluoromethoxy)phenyl]-1H-pyrazol-4-yl]-N-cyclopropyl-3-pyridinecarboxamide (Compound 1), 2-chloro-5-[1-[2-chloro-4-[1,2,2,2-tetrafluoro-1-(trifluoromethyl)ethyl]-6-(trifluoromethyl)phenyl]-1H-pyrazol-4-yl]-N-cyclopropyl-3-pyridinecarboxamide (Compound 2), tigolaner, fluralaner, afoxolaner (WO2009126668), sarolaner, lotilaner, fluxametamide, pyriprole, and fipronil.

6. The liquid formulation according to claim 1, having an active compound content of 1-60% (w/w).

7. The liquid formulation according to claim 1, comprising at least 10% (w/w) triethyl phosphate.

8. The liquid formulation according to claim 7, comprising 10 to 95% (w/w) triethyl phosphate.

9. The liquid formulation according to claim 1, comprising a cosolvent.

10. The liquid formulation according to claim 9, comprising a cosolvent selected from the group consisting of 1-methoxy-2-propyl acetate, 2-methoxy-1,3-dioxolane, 1-methoxy-2-butanol, 3,4-hexanedione, 2-heptanone, 2,3-pentadione, 3-hexanone, acetone, laurocapram, ethyl acetate, 1-dodecyl-2-pyrrolidinone, 2-pentanone, 3-pentanone, 3-methyl-2-butanone, cyclohexanone, propylene glycol, polyethylene glycol, triacetine, limonene, medium-chain triglycerides, ethyl oleate, triethyl citrate, ethylene glycol, 6-methyl-2,4-heptanedione, 2-methoxy-1-propanol, tert-butanol, 1-butanol, tetraglycol, isopropanol, 2-amino-6-methylheptane, isosorbide dimethyl ether, diethylene glycol monoethyl ether, solketal, diethyl carbonate, 3,5-heptanedione, 2,3-heptanedione, ethanol, 2-phenoxyethanol, diethyl phthalate, tributyl 2-acetylcitrate, 2,6-dimethylpyridine, tris-(2-ethylhexyl) phosphate, 4-methyl-2-pentanone, propylene glycol monoethyl ether acetate, octyldodecanol, and 6-methyl-3,5-heptanedien-2-one.

11. The liquid formulation according to claim 9, comprising 1 to 85% (w/w) cosolvent.

12. The liquid formulation according to claim 1 for use for controlling parasites in/on animals.

13. The liquid formulation according to claim 2, wherein the fluorine-containing active compound comprises at least one fluorine atom per 160 u of the molecular weight.

14. The liquid formulation according to claim 2, wherein the fluorine-containing active compound comprises at least one fluorine atom per 100 u of the molecular weight.

15. The liquid formulation according to claim 4, wherein $R^1$ represents $C_1$-$C_6$-alkyl, substituted $C_1$-$C_2$-alkyl, methyl, or H.

16. The liquid formulation according to claim 15, wherein $R^1$ represents H.

* * * * *